United States Patent
Cailleteau

(10) Patent No.: US 9,949,862 B2
(45) Date of Patent: Apr. 24, 2018

(54) POUCH COMPRISING A SAFETY VALVE

(71) Applicant: M3AT SA

(72) Inventor: Benoît Cailleteau, Blonay (CH)

(73) Assignee: M3AT SA (CH)

( * ) Notice: Subject to any disclaimer, the term of this patent is extended or adjusted under 35 U.S.C. 154(b) by 0 days.

(21) Appl. No.: 15/328,970

(22) PCT Filed: Jul. 29, 2015

(86) PCT No.: PCT/EP2015/067362
§ 371 (c)(1),
(2) Date: Jan. 25, 2017

(87) PCT Pub. No.: WO2016/016296
PCT Pub. Date: Feb. 4, 2016

(65) Prior Publication Data
US 2017/0209296 A1 Jul. 27, 2017

(30) Foreign Application Priority Data

Jul. 29, 2014 (FR) .................................... 14 57343

(51) Int. Cl.
*B65D 30/24* (2006.01)
*A61F 5/44* (2006.01)
(Continued)

(52) U.S. Cl.
CPC .............. *A61F 5/4405* (2013.01); *A61J 19/06* (2013.01); *B32B 1/02* (2013.01); *B32B 7/045* (2013.01);
(Continued)

(58) Field of Classification Search
CPC .......... A61F 5/4405; A61J 19/06; B32B 1/02; B32B 7/045; B32B 27/08; B32B 27/32; B32B 2307/7265; B32B 2439/40
(Continued)

(56) References Cited

U.S. PATENT DOCUMENTS 4,604,095 A * 8/1986 Samuelsen ............ A61F 5/4405
604/323
5,745,926 A * 5/1998 Cailleteau ................ A61F 5/44
383/44
(Continued)

FOREIGN PATENT DOCUMENTS

EP 0 117 016 4/1987
EP 748620 A1 * 12/1996
(Continued)

OTHER PUBLICATIONS

International Search Report dated Oct. 20, 2015 for corresponding international patent application No. PCT/EP2015/067362.

*Primary Examiner* — Jes F Pascua
(74) *Attorney, Agent, or Firm* — Fay Sharpe LLP; James E. Scarbrough

(57) ABSTRACT

A pouch (10) comprises a flexible bag (12) having an opening (12a) at one end, and a safety valve arranged inside the bag (12) to substantially prevent the content of the bag (12) leaving through the opening (12a). The valve comprises a first pair of sheets (22) and a second pair of sheets (24) that are bonded together locally at a plurality of spaced-apart primary bonding points (25), and a third pair of sheets (26), the first, second, and third pairs of sheets (22, 24, and 26) being bonded together locally at a plurality of spaced-apart secondary bonding points (27). The distance between the primary bonding points (25) and the distal end of the sheets of the second pair of sheets (24) varies along a transverse axis (Dt) of the bag (12).

7 Claims, 3 Drawing Sheets

(51) Int. Cl.
*A61J 19/06* (2006.01)
*B32B 1/02* (2006.01)
*B32B 7/04* (2006.01)
*B32B 27/08* (2006.01)
*B32B 27/32* (2006.01)

(52) U.S. Cl.
CPC .............. *B32B 27/08* (2013.01); *B32B 27/32* (2013.01); *B32B 2307/7265* (2013.01); *B32B 2439/40* (2013.01)

(58) Field of Classification Search
USPC .................................................. 383/44, 100
See application file for complete search history.

(56) References Cited

U.S. PATENT DOCUMENTS

| | | | | |
|---|---|---|---|---|
| 5,946,738 | A * | 9/1999 | Cailleteau | A61F 5/4404 4/144.1 |
| 8,764,716 | B2 * | 7/2014 | Christensen | A61F 5/4405 604/326 |
| 9,119,727 | B2 * | 9/2015 | Hannan | A61F 5/4405 |
| 9,592,170 | B2 * | 3/2017 | Cailleteau | A61F 5/44 |
| 2003/0014023 | A1 * | 1/2003 | Kanbara | A61F 5/441 604/333 |
| 2005/0273065 | A1 * | 12/2005 | Lillegaard | A61F 5/4404 604/332 |
| 2009/0082743 | A1 * | 3/2009 | Buglino | A61F 5/4405 604/335 |
| 2014/0163497 | A1 * | 6/2014 | Hannan | A61F 5/4405 604/344 |

FOREIGN PATENT DOCUMENTS

| | | | | |
|---|---|---|---|---|
| EP | 847742 | A1 * | 5/1998 | |
| EP | 847741 | A1 * | 6/1998 | |
| EP | 1695678 | A1 * | 8/2006 | ............... A61F 5/44 |
| FR | 2995210 | | 9/2012 | |
| FR | 1457343 | | 7/2014 | |
| GB | 2441114 | | 8/2006 | |
| GB | 2441114 | A * | 2/2008 | ........... A61F 5/4405 |
| JP | 10297651 | A * | 11/1998 | ........... A61F 5/4404 |

* cited by examiner

POUCH COMPRISING A SAFETY VALVE

BACKGROUND OF THE INVENTION

The present invention relates to a pouch comprising a flexible bag having an opening at one end, and a safety valve arranged inside the bag to substantially prevent the content of the bag from leaving through the opening.

Pouches of this type are known, e.g. from European patents Nos. 0 748 620 or 0 847 742. They are used to receive substances generally in liquid form, in particular waste of human or animal origin such as urine or vomit.

Such pouches are commonly made from thin sheets of plastics material (e.g. polyethylene) or of other flexible materials. They include a safety valve arranged inside the bag to substantially prevent the content of the bag leaving through the opening, e.g. when the pouch is accidentally turned upside-down.

Such a valve comprises at least two nested pairs of sheets that are locally bonded together at a plurality of bonding points which are aligned parallel to and in the vicinity of one of the (rectilinear or substantially rectilinear) distal end and which are equally spaced. For example, the sheets are thin sheets of plastics material, and the aligned bonding points are made by locally melting the plastics material.

With such a configuration, a liquid trapped in the bag cannot in principle leave the space between the walls of the bag and the outer pair of sheets of the valve. Furthermore, since the valve has a plurality of overlapping pairs of sheets, if a small quantity of liquid penetrates between the outer pair of sheets and the pair of sheets nested within, the liquid will tend to remain trapped between these two pairs of sheets.

After numerous tests relating to the arrangement of the bonding points, the inventor has identified the fact that the spacing between the bonding points plays a crucial role in the operation of the valve.

Specifically, the arrangement of the bonding points needs to be selected in such a manner as to obtain a good compromise between two conflicting objectives: firstly, facilitating the passage of the liquid when it is inserted into the pouch, and secondly, impeding or preventing the passage of the liquid after it has been trapped in the bag.

The inventor has discovered that the valve's ability to impede or prevent the passage of the liquid trapped in the pouch depends on the spacing between the bonding points in the direction parallel to the opening, i.e. in the direction perpendicular to the direction in which liquid is inserted into the pouch.

However, in pouches of the type mentioned above, the bonding points are merely aligned parallel to the distal end of the sheets, and the spacing between the bonding points in the direction perpendicular to the direction for inserting liquid is small, so as to limit leaks of the liquid trapped in the bag.

That configuration presents drawbacks.

Indeed, the small spacing between the bonding points tends to limit the passage of the liquid while it is being inserted into the pouch, which may impede proper use of the pouch.

Furthermore, when the liquid contains solid elements (solid elements in vomit, clots of blood in urine, etc.), the bonding points can impede or even prevent those solid elements from passing through.

OBJECT AND SUMMARY OF THE INVENTION

The present invention seeks to remedy those drawbacks.

The invention seeks to propose a pouch in which the safety valve makes it easier for solid elements to pass between the bonding points.

This object is achieved by a pouch comprising a flexible bag having an opening at one end and a safety valve arranged inside the bag to substantially prevent the content of the bag leaving via the opening, the valve comprising a first pair of sheets, each sheet of the first pair of sheets having a proximal end that is secured to a wall of the bag and a distal end opposite the proximal end along a longitudinal axis of the bag, a second pair of sheets, each sheet in the second pair of sheets extending inside the first pair of sheets and having a proximal end situated in the vicinity of the opening and a distal end closer to the opening along said longitudinal axis than the distal end of the sheets of the first pair of sheets, and a third pair of sheets, each sheet of the third pair of sheets extending inside the second pair of sheets and having a proximal end in the vicinity of the opening and a distal end closer to the opening along said longitudinal axis than the distal end of the sheets of the second pair of sheets, wherein the sheets of the first pair of sheets and of the second pair of sheets are locally bonded together in the vicinity of the distal end of the sheets of the second pair of sheets at a plurality of primary bonding points that are spaced apart from one another and that do not bond the sheets of the third pair of sheets with the sheets of the first or the second pairs of sheets, the sheets of the first, second, and third pairs of sheets are locally bonded together by a plurality of secondary bonding points that are spaced apart from one another, and the distance between the primary bonding points and the distal end of the sheets of the second pair of sheets varies along a transverse axis of the bag.

With this configuration, it is possible both to conserve small spacing between the primary bonding points along the transverse axis (i.e. along the axis perpendicular to the axis for inserting matter into the pouch), which impedes or prevents passing any liquid already trapped in the pouch, and also to provide larger spaces between the primary bonding points, thereby facilitating the passage of solid elements. In the meaning of the present description, the term "space" or "distance" between two neighboring bonding points means the length of the straight line segment between those two bonding points. Thus, the pouch may be used more hygienically when it is used for receiving a generally liquid mixture containing solid elements, such as vomit or urine containing calculi. Furthermore, when the pouch is used for receiving an emulsion of two liquids, one of which is dense, e.g. urine containing blood or blood clots, passage of the denser liquid is facilitated, thereby enabling the pouch to be used more hygienically.

According to one possibility, the primary bonding points comprise a first set of primary bonding points aligned parallel to the distal end of the sheets of the second pairs of sheets, and a second set of primary bonding points further away from said distal end than the primary bonding points of the first set.

The fabrication of the pouch is thus simplified, since it suffices to provide two lines of primary bonding points that are offset from each other forming respectively the first set and the second set, one of which is parallel to the distal end of the sheets of the second pair of sheets.

Furthermore, compared with a configuration in which all of the primary bonding points are aligned in parallel in the vicinity of the distal end of the sheets, the appearance of any undesirable deformation or shrinkage of material associated with the presence of the primary bonding points, which would otherwise degrade the liquidtightness of the valve, is limited.

According to one possibility, the primary bonding points of the second set are arranged in a staggered configuration relative to the primary bonding points of the first set.

In this way, the deformation in the material of the sheets is distributed uniformly. The liquidtightness and the strength of the valve are thus improved.

According to the invention, the valve has a third pair of sheets, each sheet in the third pair of sheets extending inside the second pair of sheets, and having a proximal end in the vicinity of the opening and a distal end that is closer to the opening along said longitudinal axis than are the distal end of the sheets of the second pair of sheets, Because of the presence of the third pair of sheets and of the secondary bonding points, the liquidtightness of the valve is further improved, since the third pair of sheets and its secondary bonding points constitute an additional impediment to the passage of any liquid that has been trapped in the bag.

According to the invention, the primary bonding points locally bond together the sheets of the first and second pairs of sheets and the secondary bonding points locally bond together the sheets of the first, second, and third pairs of sheets.

The liquidtightness of the valve is thus further improved.

According to one possibility, the distance between the secondary bonding points and the distal end of the sheets of any of the pairs of sheets varies along said transverse axis.

According to one possibility, the secondary bonding points comprise a first set of secondary bonding points aligned parallel to the distal end of the sheets of any one of the pairs of sheets, and a second set of secondary bonding points further away from said distal end than the secondary bonding points of the first set.

According to one possibility, the secondary bonding points of the second set are arranged in a staggered configuration relative to the secondary bonding points of the first set.

The above-mentioned advantages relating to the primary bonding points are thus likewise to be found for the secondary bonding points.

According to one possibility, the spacing between two neighboring primary bonding points and the spacing between two neighboring secondary bonding points increases in the same direction along said transverse axis.

The pouch of the invention, as defined above in its various embodiments, makes it possible to obtain the following effects.

Since large spaces are left between the primary bonding points, the passage of solid elements is made much easier. Furthermore, when the pouch is used for receiving an emulsion of two liquids, one of which is dense, e.g. urine containing blood or blood clots, passage of the denser liquid is facilitated. This enables the pouch to be used more hygienically.

Furthermore, when the pouch is used for receiving an emulsion of two liquids, e.g. urine containing blood or blood clots, it becomes easier to separate the liquids. In particular, when the liquids are of significantly different densities, and when the pouch is tilted towards the horizontal (i.e. so that its transverse axis becomes inclined at an angle in the range about 30° to about 60° relative to the vertical), and in such a manner that the bonding points that are spaced the furthest apart are lower down, then the liquids are separated by gravity.

BRIEF DESCRIPTION OF THE DRAWINGS

The invention will be well understood and its advantages will appear better upon reading the following detailed description of embodiments shown as non-limiting examples. The description refers to the accompanying drawings, in which.

DETAILED DESCRIPTION OF THE INVENTION

Figure 1:
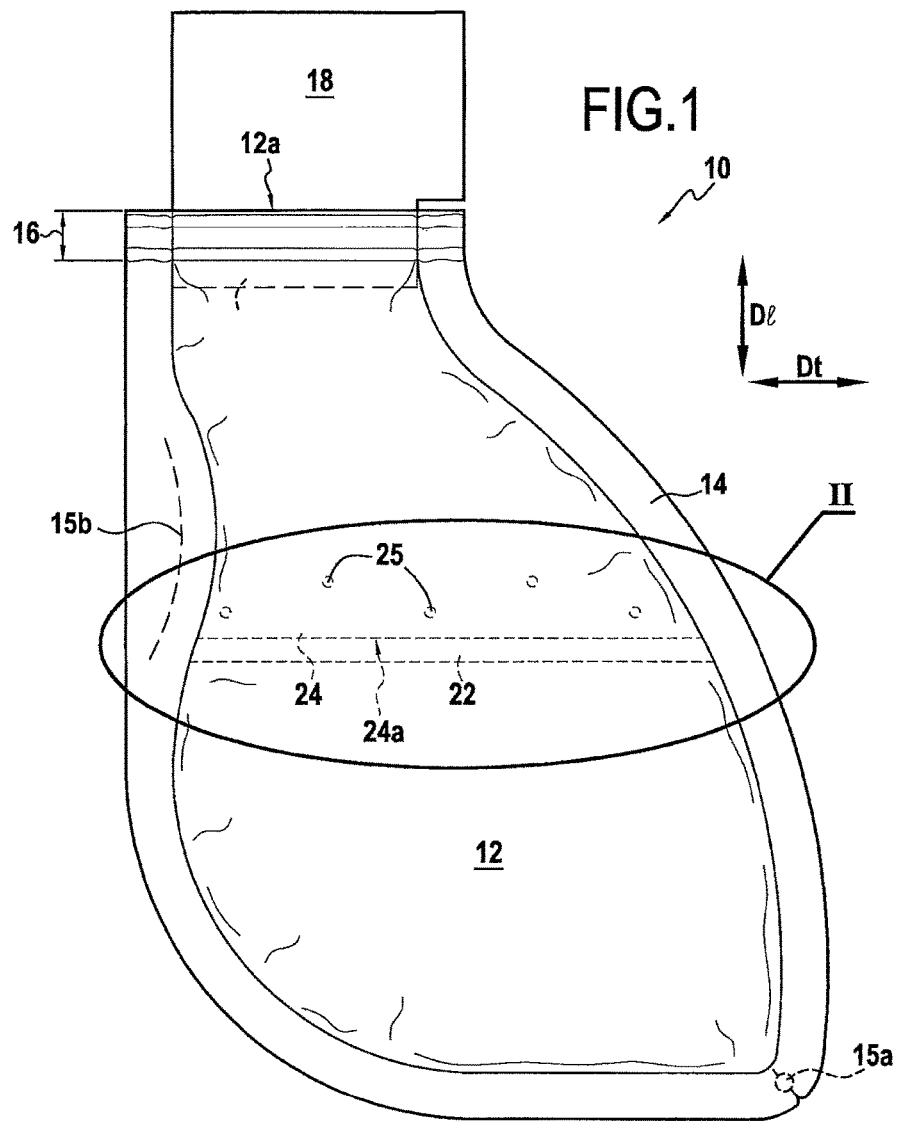
FIG. 1 is a view of a pouch according to a first embodiment, in its flat configuration.

The pouch 10 shown in FIG. 1 comprises a flexible bag 12. In particular, the bag is made from two thin sheets of plastics material that are cut out in suitable manner and welded together over almost all of their outline, by means of a weld line 14. The bag 12 has an opening 12a formed by an interruption in the weld line 14 so as to enable the space inside the bag to communicate with the outside.

In the example shown, this opening is formed at the free end of a neck portion 16 of the bag, where the width of the bag is reduced.

The bag 12 may pass from a flat configuration for easy storage to an in-use configuration in which it can receive waste.

By way of example, the sheets forming the bag are made of flexible plastics material, such as polyethylene.

The pouch comprises a reinforcing collar 18 that is secured through the opening 12a and that protrudes outside of the bag.

The collar 18 may be of any suitable shape, provided that it can be secured to the bag 12 through its opening 12a and that it can pass from a flat configuration to an in-use configuration in which it provides a channel for inserting waste. By way of example, collars suitable for this purpose are described in European patent No. 0 847 742, or in French patent application No. 2 995 210.

It can also be seen in FIG. 1 that, in a region opposite the opening, the weld line 14 has a line of weakness 15a, e.g. made by microperforations in the form of dots. This line of weakness extends only over the weld line, without reaching the inside space of the bag. When the pouch is full of waste, the waste can thus be emptied by tearing the bag along the line of weakness 15a, with sufficient force to ensure that the resulting tear extends into the inside space of the bag.

Furthermore, on one of these sides close to the opening, the weld line 14 has another line of weakness 15b that can also be made by discontinuous perforations. This line is spaced apart from the inside space of the bag and it is oriented in such a manner that tearing it cannot propagate to the inside of the bag. Thus, when the pouch is full and it is desired to store it before emptying it, the line 15b may be torn so as to provide a slot enabling the pouch to be attached to a hook or the like.

As can be seen in FIG. 1, the pouch has a safety valve constituted by several internal sheets arranged against each of the walls of the pouch.

In the example shown, the valve comprises a first pair of sheets 22 that extend, along the longitudinal axis Dl of the bag 12, from the opening 12a to a middle region of the pouch, and a second pair of sheets 24 that extend inside the pair of sheets 22, the sheets of the second pair of sheets 24 being shorter than the sheets of the first pair of sheets 22.

When the bag is in its in-use configuration, the liquid is inserted substantially parallel to the longitudinal axis Dl of the bag 12.

The sheets extend over the entire width of the pouch in the region where they are to be found and they are welded to one another and to the walls of the bag by the weld line 14.

In particular, the proximal end (the end close to the opening 12a) of each sheet in the first and second pairs of sheets 22 and 24 is secured to a wall of the bag 12 in the vicinity of the opening 12a, by the weld line 14.

As shown in FIG. 1, the sheets of the first pair of sheets 22 and the sheets of the second pair of sheets 24 are bonded together locally at a plurality of primary bonding points 25 in the vicinity of the (substantially rectilinear) distal end 24a of the sheets of the pair of sheets 24.

The sheets of the first and second pairs of sheets 22 and 24 may be made of plastics material (e.g. thin sheets of polyethylene). In this case, the primary bonding points 25 are made by locally melting the plastics material.

The invention relates most particularly to the arrangement of the primary bonding points 25.

Figure 2:
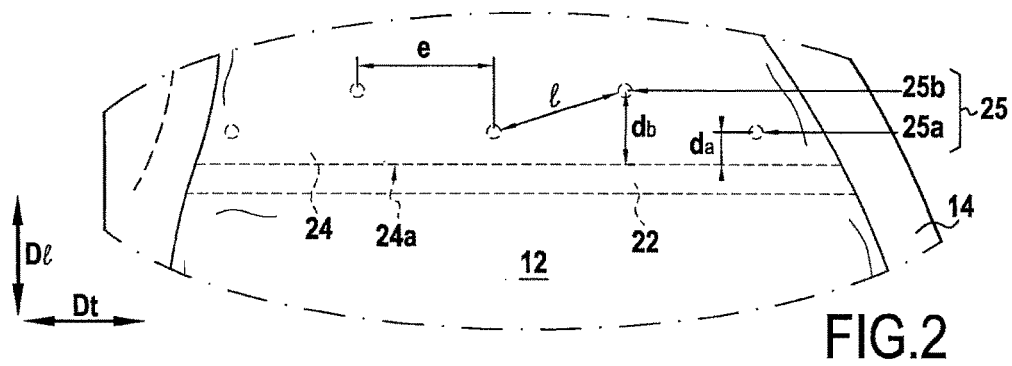
FIG. 2 is an enlargement of zone II in FIG. 1, showing the valve more clearly.

Thus, as can be seen more clearly in FIG. 2, the primary bonding points 25 are arranged in such a manner that the distance between the primary bonding points 25 and the distal end 24a of each of the sheets of the pair of sheets 24 varies along the transverse axis Dt of the bag.

In the meaning of the present description, the term "distance between the bonding points 25 and the distal end 24a" should be understood as "the shortest distance between the bonding points 25 and the distal end 24a".

In the example shown, the primary bonding points 25 comprise a first set of primary bonding points 25a aligned parallel to the distal end 24a of the sheets of the pair of sheets 24 and situated at a distance $d_a$ from the distal end 24a, and a second set of primary bonding points 25b situated at a distance $d_b$ from the distal end 24a, with the distance $d_b$ being greater than the distance $d_a$.

With this configuration, the spacing between the primary bonding points 25 parallel to the transverse axis Dt (i.e. substantially perpendicularly to the liquid insertion axis), as represented by $\underline{e}$ in FIG. 2, may be kept sufficiently small to guarantee good liquidtightness of the valve, while providing a distance l between a primary bonding point 25a and a neighboring primary bonding point 25b that is large enough to allow solid elements to pass. In other words, this configuration makes it possible to conserve liquidtightness of the valve, while also leaving sufficient space between the bonding points 25a and the bonding points 25b to allow solid elements to pass.

In addition, since the primary bonding points 25 have a second set of bonding points 25b further away from the distal end 24a than the first set, the distal end are less deformed by the presence of the bonding points and they conserve a shape that is substantially rectilinear. The liquidtightness of the valve is thus improved.

In the example shown, the bonding points 25b are aligned parallel to the distal end 24a. Nevertheless, it is possible to contemplate other configurations in which the bonding points 25b are not aligned parallel to the distal end 24a, or indeed are not aligned.

In the example shown, the bonding points 25b are arranged in a staggered configuration relative to the bonding points 25a. In other words the bonding points 25b are aligned parallel to the distal end 24a and offset relative to the bonding points 25a. In this case, the spacing parallel to the transverse axis Dt between any two adjacent bonding points 25a and the spacing between any two bonding points 25b parallel to the transverse axis Dt are identical.

With this configuration, any deformation in the material of the sheets of the first and second pairs 22 and 24 is distributed uniformly. The liquidtightness and the strength of the valve are thus improved.

Nevertheless, these spacings could equally well be different, without thereby going beyond the scope of the invention.

Figure 3:
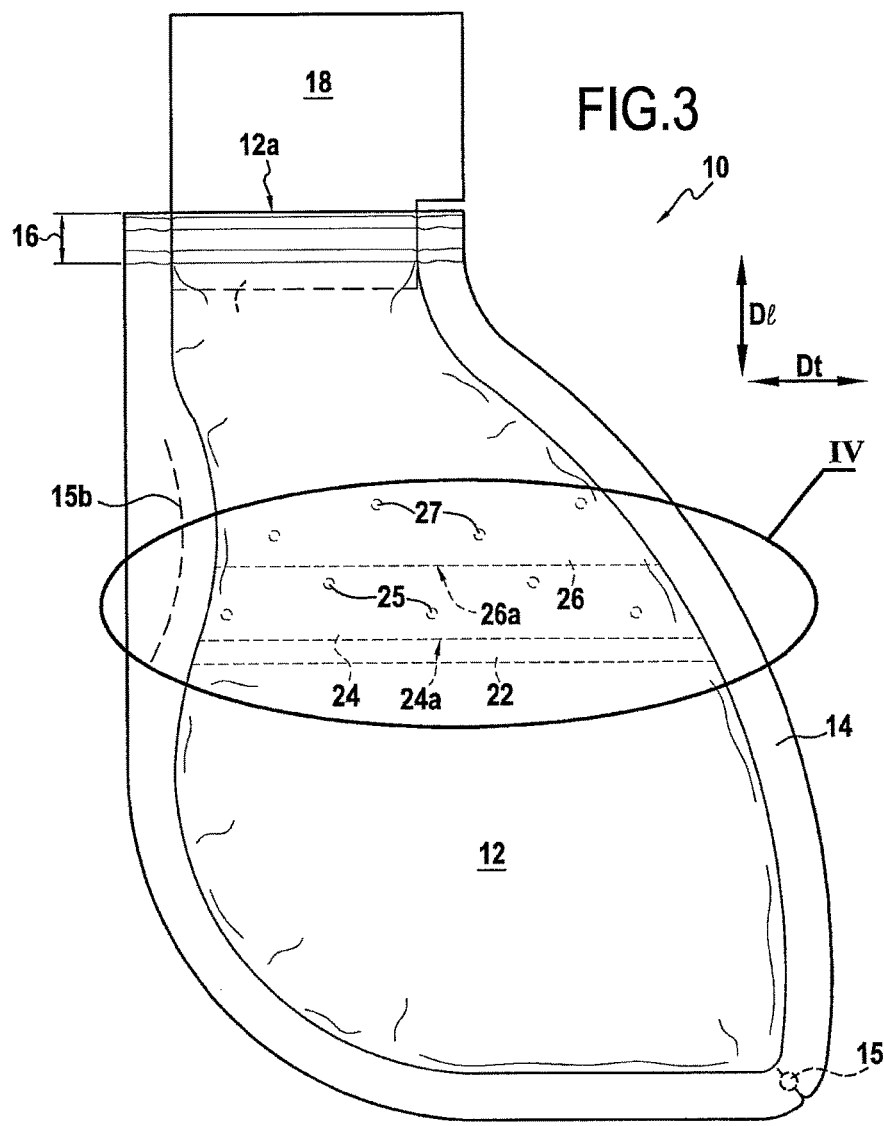
FIG. 3 is a view of a pouch according to a second embodiment, in its flat configuration.

In a second embodiment, shown in FIG. 3, the valve also has a third pair of sheets 26 extending across the entire width of the pouch in the regions where they are to be found, and welded to the walls of the bag by the weld line 14. In particular, the proximal ends (closer to the opening 12a) of the sheets of the pair of sheets 26 are secured to a wall of the bag in the vicinity of the opening 12a by the weld line 14.

The third pair of sheets 26 extends inside the pair of sheets 24, the sheets of the third pair of sheets 26 being shorter than the sheets of the pair of sheets 24. The sheets of the first and second pairs of sheets 22 and 24 are locally bonded together by the primary bonding points 25, as described above.

The first, second, and third pairs of sheets 22, 24, and 26 are locally bonded together at a plurality of secondary bonding points 27 in the vicinity of the distal end 26a of the pair of sheets 26.

The sheets of the third pair of sheets 26 may be made of plastics material (e.g. thin sheets of polyethylene). In this case, the secondary bonding points 27 are made by locally melting the plastics material.

The sheets of the third pair of sheets 26 extend in an inside volume of the bag 12 as defined by the sheets of the second pair of sheets 24.

It can be understood from the above that the primary bonding points 25 bond together locally the sheets of the first and second pairs of sheets 22 and 24 only, and that the secondary bonding points 27 bond together locally the sheets of the first, second, and third pairs of sheets 22, 24, and 26. The primary bonding points 25 do not bond together the sheets of the third pair of sheets 26 and the sheets of the first or second pairs of sheets 22 or 24. The primary bonding points 25 secure the sheets of the first and second pairs of sheets 22 and 24 to one another, the sheets of the third pair of sheets 26 not being secured to the sheets of the first and second pairs of sheets 22 and 24 by the primary bonding points 25. In addition, since the distance between the primary bonding points 25 and the distal end 24a of the sheets of the pair of sheets 24 varies along the transverse axis Dt of the bag, as described above, the passage of solid elements through the valve is facilitated.

The secondary bonding points 27 secure the sheets of the first, second, and third pairs of sheets 22, 24, and 26 to one another.

Figure 4:
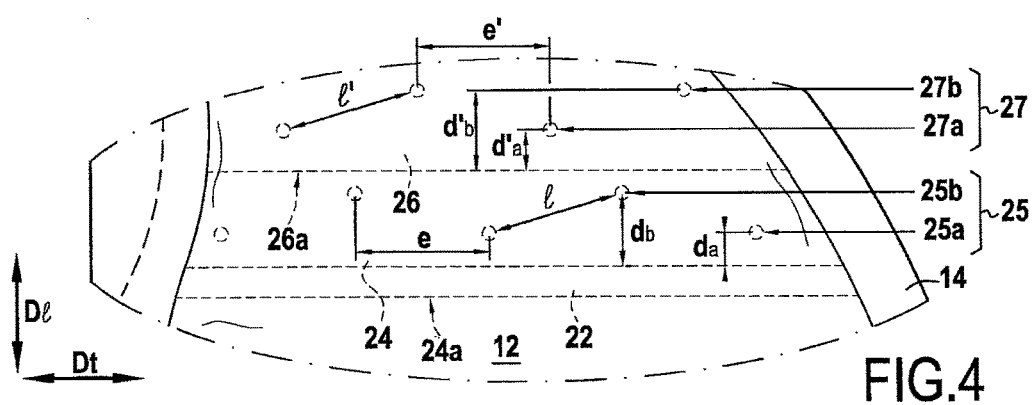
FIG. 4 is an enlargement of zone IV in FIG. 3, showing the valve more clearly.

As can be seen more clearly in FIG. 4, the secondary bonding points 27 are arranged in such a manner that the distance between the secondary bonding points 27 and the distal end 26a of the sheets of the pair of sheets 26 varies along the transverse axis Dt of the bag 12.

In the meaning of the present description, the term "the distance between the bonding points 27 and the distal end 26a" should be understood as being the "shortest distance between the bonding points 27 and the distal end 26a".

The secondary bonding points 27 comprise a first set of secondary bonding points 27a aligned parallel to the distal end of the sheets of any one of the pairs of sheets, and a second set of secondary bonding points 27b further away from the distal end than the secondary bonding points 27a. For example, and as shown in FIG. 4, the secondary bonding points 27a are situated at a distance $d'_a$ from the distal end 26a of the sheets of the pair of sheets 26, and the bonding points 27b are situated at a distance $d'_b$ from the distal end 26a, the distance $d'_b$ being greater than the distance $d'_a$.

With this configuration, the spacing between the secondary bonding points 27 parallel to the transverse axis Dt (i.e. substantially perpendicularly to the liquid insertion direction), as shown in FIG. 4, may be kept sufficiently small to guarantee good liquidtightness of the valve, while leaving a distance l' between a secondary bonding point 27a and a neighboring secondary bonding point 27b that is large enough to allow solid elements to pass.

Thus, solid elements can pass between the secondary bonding points 27a and 27b (spacing e' and distance l'), and then between the primary bonding points 25a and 25b (spacing e and distance l), as described above.

In other words, this configuration serves to further improve the liquidtightness of the valve, while leaving sufficient space between the bonding points to allow solid elements to pass.

According to one possibility, and as shown in FIG. 4, the spacing e' may be substantially equal to the spacing e.

Nevertheless, it may also be advantageous to select a spacing e' that is different from the spacing e.

For example, it is possible to select a spacing e' that is slightly greater than the spacing e. Thus, when liquid is being inserted, since the secondary bonding points 27 are spaced further apart, the liquid does not back up against the secondary bonding points 27 and can progress to the primary bonding points 25 that are situated further down, and then to the inside of the bag 12. Furthermore, after the liquid has been inserted into the bag, any passage of the liquid towards the outside of the bag 12 is initially impeded by the primary bonding points 25 which are spaced closer together and thus more strongly impede any leakage of liquid.

Naturally, in order to enable the secondary bonding points 27 to continue to contribute to the liquidtightness of the valve, the spacing e' must not be too great or excessively greater than the spacing e.

It is also possible to select a spacing e' that is slightly smaller than the spacing e. Thus, after the liquid has been inserted into the pouch, any passage of the liquid towards the outside of the bag 12 is impeded initially by the primary bonding points 25, and subsequently by the third pair of sheets 26 and the secondary bonding points 27 that impede leakage of the liquid more strongly since they are closer together.

Furthermore, since the secondary bonding points 27 comprise a second set of bonding points 27b further away from the distal end 26a than the first set, the distal end is less deformed by the presence of bonding points and conserve a shape that is substantially rectilinear. The liquidtightness of the pouch is thus improved.

In the example shown, the bonding points 27b are aligned parallel to the distal end 26a. Nevertheless, it is possible to contemplate other configurations in which the bonding points 27b are not aligned parallel to the distal end 26a, or indeed are not aligned.

In the example shown, the bonding points 27b are arranged in a staggered configuration relative to the bonding points 27a. I.e. the bonding points 27b are aligned parallel to the distal end 26a and they are offset relative to the bonding points 27a. In this case, the spacing between any two neighboring bonding points 27a parallel to the transverse axis Dt, and the spacing between any two bonding points 27b parallel to the transverse axis Dt are identical.

With this configuration, any deformation of the material of the sheets of the first, second, and third pairs of sheets 22, 24, and 26 is distributed uniformly. The liquidtightness and the strength of the valve are thus improved.

Nevertheless, these spacings could equally well be different, without thereby going beyond the scope of the invention.

Figure 5:
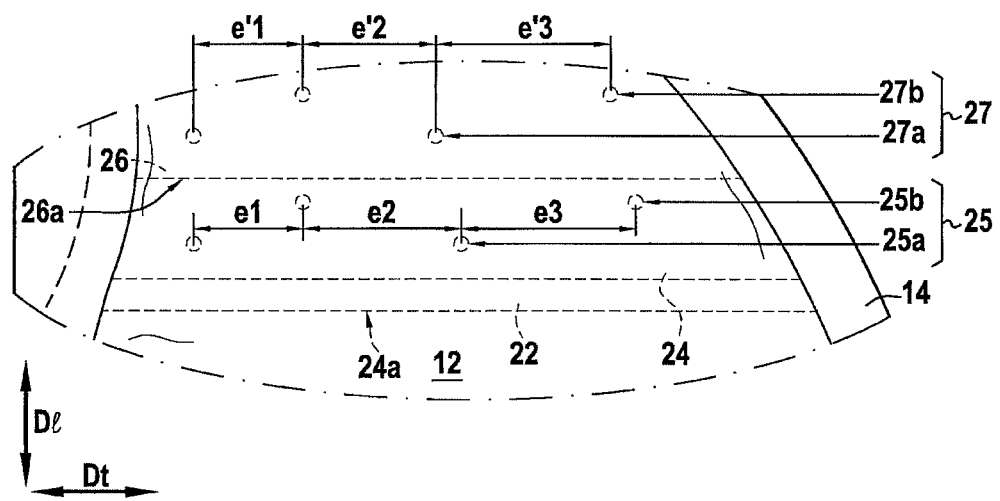
FIG. 5 is an enlargement of the same zone, showing the valve in a third embodiment.

In a third embodiment, shown in FIG. 5, the bonding points 25 and 27 are arranged in such a manner that the spacing between two successive neighboring primary bonding points 25 increases in a given direction along the transverse axis Dt starting from the edge d' of the bag 12 formed by the weld line 14 in the proximity of the line of weakness 15b and going to the other edge of the bag 12 formed by the weld line 14, and the spacing between two successive neighboring secondary bonding points 27 increases in the same direction along the transverse axis Dt.

More precisely, and as shown in FIG. 5, the successive spacings $e_1$, $e_2$, $e_3$, . . . between successive neighboring primary bonding points 25 are such that:

$$e_1 \leq e_2 \leq e_3 \leq \ldots$$

Likewise, the successive spacings $e'_1$, $e'_2$, $e'_3$, . . . between successive neighboring secondary bonding points 27 are such that:

$$e'_1 \leq e'_2 \leq e'_3 \leq \ldots$$

With this configuration, when the pouch 10 is tilted towards the horizontal (i.e. such that the transverse axis Dt makes an angle in the range about 30° to about 60° relative to the vertical) and in such a manner that the most spaced-apart bonding points 25 and 27 are lower down, and when the pouch 10 is used to receive a mixture of liquids different densities, the liquids are separated by gravity, with the separation of the liquids being facilitated.

In a variant, provision may be made for only the primary bonding points 25 or only the secondary bonding points 27 to be arranged in such a manner that the spacing between two successive neighboring bonding points increases in one direction along the transverse axis Dt, without thereby going beyond the scope of the invention.

Although the present invention is described with reference to specific embodiments, it is clear that various modifications and changes may be undertaken on those embodiments without going beyond the general scope of the invention as defined by the claims. In addition, individual characteristics of the various embodiments mentioned may be combined in additional embodiments. Consequently, the description and the drawings should be considered in a sense that is illustrative rather than restrictive.

The invention claimed is:
1. A pouch comprising:
   a flexible bag having an opening at one end;
   a safety valve arranged inside the bag to substantially prevent the content of the bag leaving via the opening, said valve comprising:

a first pair of sheets, each sheet of the first pair of sheets having a proximal end in the vicinity of the opening that is secured to a wall of the bag and a distal end opposite the proximal end along a longitudinal axis l of the bag;

a second pair of sheets, each sheet in the second pair of sheets extending inside the first pair of sheets and having a proximal end situated in the vicinity of the opening, and a distal end closer to the opening along said longitudinal axis l than the distal end of the sheets of the first pair of sheets; and a third pair of sheets, each sheet of the third pair of sheets extending inside the second pair of sheets and having a proximal end in the vicinity of the opening, and a distal end closer to the opening along said longitudinal axis l than the distal end of the sheets of the second pair of sheets;

wherein:

the sheets of the first pair of sheets and of the second pair of sheets are locally bonded together in the vicinity of the distal end of the sheets of the second pair of sheets, at a plurality of primary bonding points that are spaced apart from one another and that do not bond the sheets of the third pair of sheets with the sheets of the first or the second pairs of sheets; and the sheets of the first, second, and third pairs of sheets are locally bonded together by a plurality of secondary bonding points that are spaced apart from one another;

the distance between the primary bonding points and the distal end of the sheets of the second pair of sheets varies along a transverse axis of the bag.

2. A pouch according to claim 1, wherein the primary bonding points comprise:

a first set of primary bonding points aligned parallel to the distal end of the sheets of the second pairs of sheets; and a second set of primary bonding points further away from said distal end than the primary bonding points of the first set.

3. A pouch according to claim 2, wherein the primary bonding points of the second set are arranged in a staggered configuration relative to the primary bonding points of the first set.

4. A pouch according to claim 1, wherein the distance between the secondary bonding points and the distal end of the sheets of any of the pairs of sheets varies along said transverse axis.

5. A pouch according to claim 4, wherein the secondary bonding points comprise:

a first set of secondary bonding points aligned parallel to the distal end of the sheets of any one of the pairs of sheets; and a second set of secondary bonding points further away from said distal end than the secondary bonding points of the first set.

6. A pouch according to claim 5, wherein the secondary bonding points of the second set are arranged in a staggered configuration relative to the secondary bonding points of the first set.

7. A pouch according to claim 1, wherein the spacing between two neighboring primary bonding points and the spacing between two neighboring secondary bonding points increases in the same direction along said transverse axis.

\* \* \* \* \*